(12) United States Patent
Ume et al.

(10) Patent No.: US 8,256,296 B2
(45) Date of Patent: Sep. 4, 2012

(54) METHODS AND SYSTEMS FOR DETECTING DEFECTS IN WELDED STRUCTURES UTILIZING PATTERN MATCHING

(75) Inventors: Ifeanyi Charles Ume, Atlanta, GA (US);
Renfu Li, Johnes Creek, GA (US);
Matthew Rogge, Atlanta, GA (US);
Tsun-Yen Wu, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 497 days.

(21) Appl. No.: 12/534,296

(22) Filed: Aug. 3, 2009

(65) Prior Publication Data

US 2011/0023609 A1    Feb. 3, 2011

(51) Int. Cl.
*G01N 29/00*    (2006.01)
(52) U.S. Cl. .......... 73/627; 73/622; 73/600; 73/602
(58) Field of Classification Search ............ 73/596–600, 73/602, 622, 627
See application file for complete search history.

(56) References Cited

U.S. PATENT DOCUMENTS

| | | | |
|---|---|---|---|
| 3,436,958 A | 4/1969 | Proctor | |
| 3,575,044 A | 4/1971 | Gibbs et al. | |
| 3,585,851 A | 6/1971 | Walther | |
| 3,693,158 A | 9/1972 | Uthe | |
| 3,791,199 A | 2/1974 | Toth et al. | |
| 4,298,808 A | 11/1981 | Hill | |
| 4,522,064 A | 6/1985 | McMillan | |
| 4,531,409 A * | 7/1985 | Koch et al. ................. | 73/588 |
| 4,869,109 A * | 9/1989 | Miglianico et al. .......... | 73/602 |
| 5,283,418 A | 2/1994 | Bellows et al. | |
| 5,475,613 A | 12/1995 | Itoga et al. | |
| 5,476,010 A | 12/1995 | Fleming et al. | |
| 5,544,256 A | 8/1996 | Brecher et al. | |
| 5,619,998 A | 4/1997 | Abdel-Malek et al. | |
| 5,674,415 A | 10/1997 | Leong et al. | |
| 5,724,138 A | 3/1998 | Reich et al. | |
| 5,764,859 A | 6/1998 | Kim et al. | |
| 5,907,100 A | 5/1999 | Cook | |
| 5,932,123 A | 8/1999 | Marhofer et al. | |
| 6,125,705 A | 10/2000 | Johnson | |
| 6,335,504 B1 | 1/2002 | Ling et al. | |

(Continued)

OTHER PUBLICATIONS

Amara Graps An Introduction to Wavelets IEEE Computational Science and Engineering, Summer 1995, vol. 2, No. 2., Published by IEEE Computer Society, 10662 Los Vaqueros Circle, Los Alamitos, CA 90720, USA.

(Continued)

*Primary Examiner* — Helen C. Kwok
(74) *Attorney, Agent, or Firm* — Dinsmore & Shohl, LLP

(57) ABSTRACT

A method for processing ultrasonic response signals collected from a plurality of measurement locations along a weld to determine the presence of a defect in the weld may include filtering an ultrasonic response signal from each of the measurement locations to produce a filtered response signal for each of the measurement locations. Thereafter, an ultrasonic energy for each of the measurement locations is calculated with the corresponding filtered response signal. The ultrasonic energy for each measurement location is then compared to the ultrasonic energy of adjacent measurement locations to identify potential defect locations. When the ultrasonic energy of a measurement location is less than the ultrasonic energy of the adjacent measurement locations, the measurement location is a potential defect location. The presence of a defect in the weld is then determined by analyzing fluctuations in the ultrasonic energy at measurement locations neighboring the potential defect locations.

17 Claims, 7 Drawing Sheets

U.S. PATENT DOCUMENTS

| | | | |
|---|---|---|---|
| 6,484,584 B2 | 11/2002 | Johnson et al. | |
| 6,497,150 B1 | 12/2002 | Kruzic | |
| 6,532,820 B1 | 3/2003 | Fleming et al. | |
| 6,532,821 B2 | 3/2003 | Lamouche et al. | |
| 6,597,997 B2 | 7/2003 | Tingley | |
| 6,640,632 B1* | 11/2003 | Hatanaka et al. | 73/598 |
| 6,848,312 B2 | 2/2005 | Georgeson | |
| 6,857,553 B1 | 2/2005 | Hartman et al. | |
| 6,896,171 B2 | 5/2005 | Den Boer et al. | |
| 6,923,067 B2 | 8/2005 | Coen et al. | |
| 6,937,329 B2 | 8/2005 | Esmiller | |
| 6,948,369 B2 | 9/2005 | Fleming et al. | |
| 7,094,989 B2 | 8/2006 | McJunkin et al. | |
| 7,132,617 B2 | 11/2006 | Lee et al. | |
| 7,204,147 B2 | 4/2007 | Fujimoto et al. | |
| 7,234,355 B2 | 6/2007 | Dewangan et al. | |
| 7,278,315 B1* | 10/2007 | Klein et al. | 73/602 |
| 7,516,022 B2 | 4/2009 | Lee et al. | |
| 7,557,558 B2 | 7/2009 | Barrow | |
| 7,728,254 B2 | 6/2010 | D'Angelo et al. | |
| 7,784,347 B2 | 8/2010 | Messer et al. | |
| 7,851,753 B2 | 12/2010 | Uto et al. | |
| 7,926,349 B2 | 4/2011 | Sargent | |
| 2002/0017139 A1 | 2/2002 | Kluft et al. | |
| 2002/0053555 A1 | 5/2002 | Matsuyama | |
| 2003/0167616 A1 | 9/2003 | Harding et al. | |
| 2003/0200809 A1 | 10/2003 | Hatanaka et al. | |
| 2005/0230360 A1 | 10/2005 | Maev et al. | |
| 2007/0038400 A1 | 2/2007 | Lee et al. | |
| 2007/0234809 A1 | 10/2007 | Klein et al. | |
| 2008/0072674 A1 | 3/2008 | Ume et al. | |
| 2008/0210010 A1 | 9/2008 | Orth et al. | |
| 2010/0319456 A1* | 12/2010 | Ume et al. | 73/622 |
| 2011/0023610 A1* | 2/2011 | Ume et al. | 73/622 |

OTHER PUBLICATIONS

Christopher Torrence, Gilbert P. Compo A Practical Guide to Wavelet Analysis Program in Atmospheric and Oceanic Sciences, University of Colorado, Boulder, Colorado Bulletin of the American Meteorological Society, vol. 79, No. 1, Jan. 1998.

Office Action mailed Oct. 27, 2011 as it relates to U.S. Appl. No. 12/488,396.

Notice of Allowance and Allowability mailed Nov. 30, 2011 as it relates to U.S. Appl. No. 12/534,581.

Neural Networks, [Retrieved Aug. 3, 2009] Retrieved from the internet <url:http://learnartificialneuralnetworks.com>.

Back propagation Neural Network, [Retrieved Aug. 3, 2009] Retrieved from the internet <url:http://learnartificialneuralnetworks.com/backpropagation.htm>.

P.K..Simpson Foundations of Neural Networks Proceedings of the Adaptive Control Systems Technology Symposium, Oct. 24-25, 1994, pp. 16-37.

* cited by examiner

METHODS AND SYSTEMS FOR DETECTING DEFECTS IN WELDED STRUCTURES UTILIZING PATTERN MATCHING

CROSS REFERENCE TO RELATED APPLICATIONS

This specification is related to commonly assigned U.S. patent application Ser. No. 12/488,396 filed Jun. 19, 2009 entitled "METHODS AND SYSTEMS FOR DETECTING DEFECTS IN WELDED STRUCTURES" and U.S. patent application Ser. No. 12/534,581 filed Aug. 3, 2009 entitled "METHODS AND SYSTEMS FOR CLASSIFYING THE TYPE AND SEVERITY OF DEFECTS IN WELDS".

TECHNICAL FIELD

The present specification generally relates to methods and systems for detecting defects in welded structures and, more specifically, to methods and systems for detecting defects in welded structures utilizing ultrasonic inspection in conjunction with defect pattern matching.

BACKGROUND

Various welding techniques are commonly utilized to join metallic parts to produce a wide variety of articles of manufacture such as, for example, automobile components, aircraft components, heavy equipment and machinery. The quality of the weld may play an important role in the structural integrity of the welded structure in which it is employed. However, during the welding or joining operation, defects may be introduced or formed in the weld. Such defects may include blowholes, voids, porosity and insufficient weld penetration depth. Each of these defects may decrease the load bearing capacity of the welded structure. For example, some types of defects may act as stress risers or stress concentrators which may impact the static, dynamic and fatigue strength of the weld and the welded structure. Therefore, it is important to accurately detect and locate potential defects in the welds.

When welds are formed automatically, such as by an automated or robotic welding system, the quality of a weld may be assessed by destructively testing a random sampling of the welded structures that are produced. Destructive tests, such as cut-checks, may be time-consuming and may generate excess product waste. Moreover, automation of such destructive testing methodologies may not be possible.

Efforts have been made to develop various non-destructive testing techniques for detecting defects in welds. However, most of these techniques may not be easily incorporated into manufacturing environments.

Accordingly, a need exists for alternative methods and systems for detecting defects in welds.

SUMMARY

In one embodiment, a method for processing ultrasonic response signals collected from a plurality of measurement locations along a weld to determine the presence of defects in the weld may include filtering an ultrasonic response signal from each of the measurement locations to produce a filtered response signal for each of the measurement locations. Thereafter, an ultrasonic energy for each of the measurement locations may be calculated with the corresponding filtered response signal. The ultrasonic energy for each measurement location may then be compared to the ultrasonic energy of adjacent measurement locations to identify potential defect locations. When the ultrasonic energy of a measurement location is less than the ultrasonic energy of the adjacent measurement locations, the measurement location is a potential defect location. The presence of a defect in the weld may then be determined by analyzing fluctuations in the ultrasonic energy at measurement locations neighboring the potential defect locations.

In another embodiment, a method for testing a weld for the presence of defects may include inducing ultrasonic signals at multiple measurement locations along the weld and collecting a corresponding ultrasonic response signal for each of the measurement locations along the weld. Thereafter, an ultrasonic response signal from each of the measurement locations may be filtered to produce a filtered response signal for each of the measurement locations. An ultrasonic energy for each of the measurement locations may then be calculated using the filtered response signal for the corresponding measurement location. Thereafter, an ultrasonic energy distribution for the weld may be determined based on the calculated ultrasonic energy for each of the measurement locations. Local minima in the ultrasonic energy distribution may then be determined and fluctuations in the ultrasonic energy distribution around each local minimum may be analyzed to determine the presence of a defect in the weld.

In yet another embodiment, a defect detection system for determining the presence of defects in a weld may include a controller, an acoustic signal generator, an acoustic signal detector, and a positioning device. The acoustic signal generator, the acoustic signal detector and the positioning device may be electrically coupled to the controller. The controller may be programmed to: induce ultrasonic signals at multiple measurement locations along the weld with the acoustic signal generator; collect an ultrasonic response signal from each of the measurement locations with the acoustic signal detector and store the ultrasonic response signals in a memory operatively associated with the controller; filter an ultrasonic response signal from each of the measurement locations to produce a filtered response signal for the corresponding measurement locations; calculate an ultrasonic energy for each of the measurement locations with the corresponding filtered response signal; compare the ultrasonic energy for each measurement location to the ultrasonic energy of adjacent measurement locations to identify potential defect locations, wherein, when the ultrasonic energy of a measurement location is less than the ultrasonic energy of the adjacent measurement locations, the measurement location is a potential defect location; and determine the presence of a defect in the weld by analyzing fluctuations in the ultrasonic energy at measurement locations neighboring the potential defect locations.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
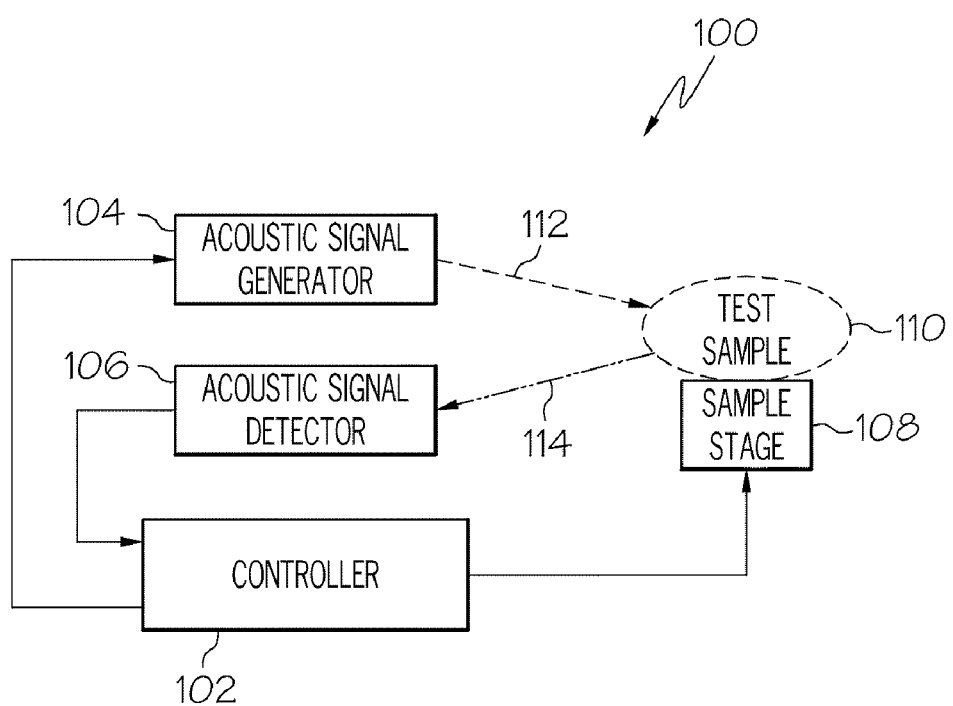
FIG. 1 is a block diagram of a defect detection system according to one or more embodiments shown and described herein.

FIG. 1 generally depicts one embodiment of a defect detection system for determining the presence and location of defects in a weld. The system may generally comprise an acoustic signal generator and an acoustic signal detector coupled to a controller. The various components of the defect detection system and methods of using the defect detection system to determine the presence and location of defects in a welded structure will be described in more detail herein.

Referring now to FIG. 1, a block diagram of a defect detection system 100 is depicted. The defect detection system 100 may generally comprise an acoustic signal generator 104, an acoustic signal detector 106 and a sample stage 108, each of which are electrically coupled to a controller 102. Accordingly, it should be understood that the solid lines and arrows shown in FIG. 1 are generally indicative of the electrical interconnectivity of the various components of the defect detection system 100. It should also be understood that the solid lines and arrows are indicative of electronic signals, such as control signals and/or data signals, propagated between the various components of the defect detection system 100. Further, it should be understood that the dashed line and arrow between the acoustic signal generator 104 and the test sample 110 is indicative of excitation signals 112 transmitted from the acoustic signal generator 104 to a test sample 110 while the dashed line and arrow between the test sample 110 and the acoustic signal detector 106 is indicative of an ultrasonic response signal 114 emitted from the test sample 110 due to the received excitation signal 112 from the acoustic signal generator 104.

In the embodiments shown and described herein the acoustic signal generator 104 may be a device operable to excite an ultrasonic signal in the test sample 110 without physically contacting the test sample. In one embodiment, the acoustic signal generator 104 may comprise a pulsed laser source operable to excite an ultrasonic signal in the test sample 110 by directing a series of laser pulses onto the surface of the test sample. In another embodiment, the acoustic signal generator 104 may comprise an electromagnetic acoustic transducer (EMAT) operable to excite an ultrasonic signal in the test sample 110 using electromagnetic fields. It should be understood that the acoustic signal generator 104 may comprise other devices suitable for generating ultrasonic signals in the test sample 110.

The acoustic signal detector 106 may generally be a device operable to sense or detect the ultrasonic response signals 114 generated in the test sample 110 without physically contacting the test sample. Accordingly, in one embodiment, the acoustic signal detector 106 may comprise an EMAT sensor operable to detect the acoustic response signal generated in the test sample 110. However, it should be understood that various other non-contact transducers and/or acoustic sensors may be used to detect the ultrasonic response signal 114.

In one embodiment (not shown), where the acoustic signal generator is an EMAT, the EMAT may be used to both excite an ultrasonic signal in the test sample and to detect the ultrasonic response signal from the test sample. Accordingly, it should be understood that a single EMAT may be used as both the acoustic signal generator and the acoustic signal detector.

In the embodiment of the defect detection system 100 shown in FIG. 1, the sample stage 108 may comprise a fixture (not shown) for mounting a test sample to the sample stage. The sample stage 108 may comprise one or more actuators (not shown), such as motors and/or stepper motors, mechanically coupled to the stage and electrically coupled to the controller 102. The controller 102, in conjunction with the actuators, may be operable to adjust the position of sample stage 108 and test sample 110 relative to the acoustic signal generator 104 and acoustic signal detector 106 such that the excitation signals 112 emitted by the signal generator may be scanned over the test sample 110 in a controlled manner.

While the embodiments shown and described herein depict the test sample as being fixtured to a moveable sample stage, it should be understood that, in other embodiments (not shown), the acoustic signal generator and the acoustic signal detector may be attached to a moveable stage or similar positioning device electrically coupled to the controller such that the acoustic signal generator and the acoustic signal detector may be adjustably positioned relative to the test sample. Accordingly, it should be understood that the defect detection device may include at least one positioning device for adjusting the relative orientation between the test sample and the acoustic signal generator and acoustic signal detector.

The controller 102 may comprise a computer operable to execute a programmed instruction set and transmit control signals to each of the components of the defect detection system 100. The controller 102 may also be operable to store data received from the acoustic signal detector 106 and analyze the stored data to determine the presence of defects in a weld. Accordingly, it should be understood that the controller 102 may comprise or be coupled to one or more memory devices (not shown) for storing the programmed instruction set and/or data received from the acoustic signal detector. The controller 102 may also be coupled to one or more audible or visual indicators, such as a display (not shown), for providing a user with a visual or audible indication of the presence and location of defects in the test sample and/or an indication of whether the test sample has passed inspection.

Figure 2:
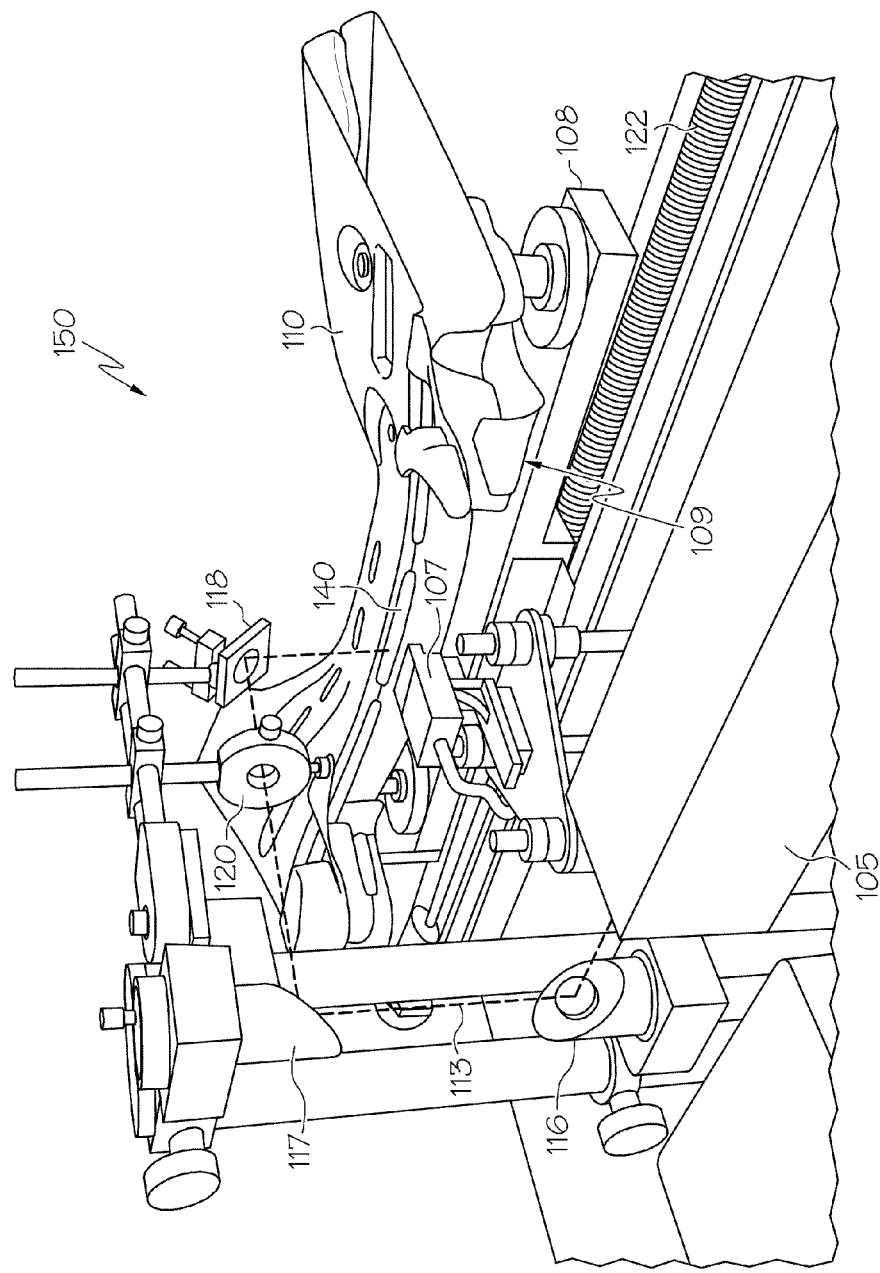
FIG. 2 depicts a defect detection system according to one or more embodiments shown and described herein.

Referring now to FIG. 2, one embodiment of a defect detection system 150 is illustrated. In this embodiment the acoustic signal generator is a pulsed laser source 105, such as an Inlite II-20 Nd:YAG pulsed laser manufactured by Continuum Lasers. The pulsed laser source 105 may have a 20 Hz pulse repetition rate and a pulse width of 10 ns. The spot size of the laser may be about 6 mm and each pulse may have an energy from about 55 mJ to about 450 mJ. The acoustic signal detector may be an EMAT sensor 107. In the embodiment depicted in FIG. 2 the EMAT sensor 107 is manufactured by BWXT Services, Inc. and comprises a four channel broadband receiver having a bandwidth from about 200 kHz to about 2.5 MHz. The EMAT sensor 107 may be coupled to the controller (not shown) with a data acquisition card, such as, for example, a Compuscope 8349 4 channel data acquisition card manufactured by GaGe Applied Technologies which has 14 bit resolution and a data sampling rate of 125 MHz. The sample stage 108 may include one or more fixturing device(s) 109, such as clamps, vices, etc. for holding test sample 110. The fixturing device and/or test sample may include one or more datums (not shown) such that test samples may be positioned on the sample stage with substantially the same orientation relative to the pulsed laser source 105 and the EMAT sensor 107. The sample stage 108 may be mounted to a stepper motor-driven lead screw 122 coupled to the controller such that the position of the sample stage may be adjusted with the controller.

In the embodiment of the defect detection system 150 shown in FIG. 2, the excitation source is the output beam 113 of the pulsed laser source 105 which is optically coupled to the test sample 110 with one or more mirrors. As depicted in FIG. 2, mirrors 116, 117 and 118 form an optical path between the output of the pulsed laser source 105 and the surface of the test sample 110 which directs the output beam 113 onto the surface of the test sample at the desired location. A lens 120 may be disposed in the optical path of the output beam 113 to focus the output beam. Additional optical elements (not shown) may also be inserted in the optical path such as, for example, collimators or other elements which may be used to shape the output beam 113 of the pulsed laser source 105. Further, while the embodiments of the defect detection system 150 shown in FIG. 2 depict the output beam 113 coupled to the test sample 110 with mirrors, it should be understood that the output beam may be directly coupled to the test sample without being first diverted or reflected by a mirror. In alternative embodiments (not shown), the output beam 113 of the pulsed laser source may be coupled to the test sample with one or more optical waveguides, such as an optical fiber or similar optical waveguides capable of guiding a laser beam.

As described herein, the pulsed laser source may be used to induce an ultrasonic signal in the test sample. Depending on the energy density or power of the output beam pulse incident on the surface of the test sample, the pulsed-laser source may be utilized to create an ultrasonic signal in either a thermoelastic mode of operation or an ablative mode of operation. For example, the thermoelastic mode of ultrasonic signal generation occurs when the power density of the output beam of the pulsed laser source is relatively low. The output beam rapidly heats a localized area on the surface of the test sample to a temperature less than the melting point of the material due to partial absorption of the laser radiation. The rapid increase in temperature is accompanied by a corresponding expansion of the heated material due to thermoelastic effects. The rapid expansion causes axis-symmetric tensile stresses to develop in the surface of the test sample. When the laser is switched off (e.g., between pulses), the heated region contracts. The expansion and contraction of the top surface of the test sample induces ultrasonic signals that propagate through the test sample.

Alternatively, the ablative mode of ultrasonic signal generation occurs when the power density of the output beam is high enough to heat the surface of the test sample to above the melting temperature of the material. The rapid heating creates axis-symmetric tensile stresses in the surface of the test sample, as described above. However, as the temperature on the surface of the sample exceeds the melting temperature, a small amount of material is vaporized and ejected from the surface of the test sample. Accordingly, in addition to the formation of tensile stresses, a normal reaction force is created against the surface of the sample as the material is ejected. The combination of the normal reaction force and the expansion and contraction of the top surface induces ultrasonic signals that propagate through the test sample. In general, ultrasonic signals generated through the ablative mode are generally stronger that those generated in the thermoelastic mode. In either mode of operation the ultrasonic signals induced in the test sample have frequency content from about 200 kHz to about MHz.

Figure 3:
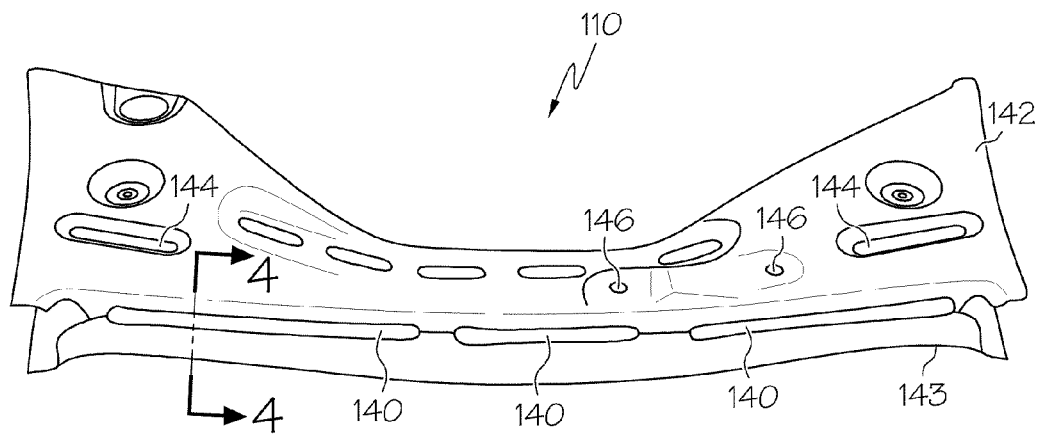
FIG. 3 depicts a test sample comprising a plurality of welds and various manufacturing features.

Referring now to FIGS. 2 and 3, the test sample 110 may generally comprise a metallic structure which comprises at least one weld 140. In the embodiment of the test sample 110 shown in FIGS. 2 and 3, the test sample 110 is a structural support member for an automobile which comprises an upper portion 142 and a lower portion 143, both of which are formed from thin plates of stamped sheet metal. The upper portion 142 may be joined to the lower portion 143 at a lap joint (e.g., the joint shown in FIG. 4) with welds 140. The test sample 110 may also comprise a plurality of manufacturing features including, for example, press marks 144 resulting from a stamping operation and various attachment holes 146 for connecting components to the structural support member.

Figure 4:
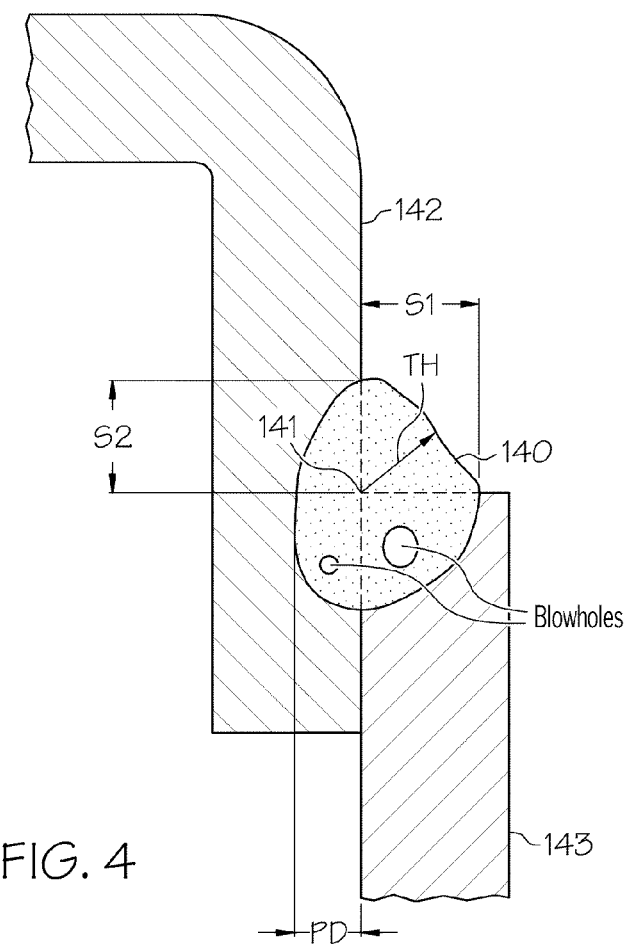
FIG. 4 depicts a cross section of a weld of the test sample of FIG. 3 illustrating various defects that may be present in the weld.

Referring now to FIG. 4 which depicts a cross section of a lap joint and weld 140 between the upper portions 142 and lower portion 143 of the test sample 110 of FIGS. 2 and 3, the weld 140 may contain one or more different types of defects including, for example, blowholes, insufficient leg length (i.e., short legs), insufficient penetration depth and/or insufficient throat thickness (i.e., short throat). A blowhole defect occurs in the weld when air or gas trapped in the weld escapes from the weld as the weld is formed or as the weld cools. The escaping air or gas leaves a void in the weld and/or forms pores in the weld, each of which may decrease the strength of the weld.

The penetration depth of a weld is defined as the distance PD which the fusion portion of the weld penetrates into the base material, such as, for example, the upper portion 142 of the test sample 110. If the penetration depth is less than a specified percentage of the thickness of the base material an insufficient penetration depth or lack-of-penetration defect occurs. In the embodiments described herein, a lack-of-penetration defect occurs when the distance PD is less than about 30% of the thickness of the upper portion 142 of the test sample. However, it should be understood that the specified percentage may be greater than 30% or less than 30% depending on the application in which the test sample 110 is employed.

The legs of a lap joint weld 140 are defined as the distance between the root 141 of the weld 140 and the toe of the weld (e.g., the point where the weld intersects the base material). The legs of the weld 140 in FIG. 4 are shown as the distances S1 and S2. In the embodiments described herein, a short leg defect is present in the weld if either of the distances S1 or S2 is less than 80% of the material thickness of either the upper portion 142 or lower portion 143 of the test sample 110. However, it should be understood that the specified percentage may be greater than 80% or less than 80% depending on the application in which the test sample 110 is employed.

The throat thickness TH is defined as the shortest distance between the root 141 of the weld 140 and the surface of the weld, as shown in FIG. 4. A short throat defect occurs when the throat thickness of the weld 140 is less than a specified percentage of the thickness of the base material. In the embodiments shown and described herein, a short throat occurs when the throat thickness TH is less than about 70% of the thickness of either the upper portion 142 or lower portion 143 of the test sample. However, it should be understood that the specified percentage may be greater than 70% or less than 70% depending on the application in which the test sample 110 is employed.

Ultrasonic signals induced in the thin plates which comprise the upper portion 142 and the lower portion 143 of the test sample 110 by operating the pulsed laser source in either the thermoelastic mode or ablative mode produce a series of ultrasonic Lamb waves which propagate through the test sample. The Lamb waves may be multi-modal with each mode defined by a set of frequency and wavelength pairs. Due to the different frequencies and wavelengths, each mode of the Lamb wave may react differently to different types of defects encountered in the test sample. For example, for a given type of defect, a first mode defined by a first set of frequency and wavelength pairs may be reflected by the defect while a second mode having a second set of frequency and wavelength pairs may be transmitted through the defect (i.e., the defect does not affect the second mode). Accordingly, different modes of the induced Lamb waves may be sensitive to different types of defects and, by collecting and analyzing an ultrasonic response signal from the test sample, the presence of different types of defects in the test sample may be determined, as will be described in more detail herein.

Referring now to FIG. 2, in order to determine the presence of defects in a weld on a test sample, the test sample 110 may be positioned on the sample stage 108 and attached to the sample stage 108 with one or more fixturing devices 109. The pulsed laser source 105 and EMAT sensor 107 may be positioned such that the EMAT sensor 107 collects an acoustic response signal either transmitted through the weld or reflected by the weld.

For example, in one embodiment, when an acoustic response signal transmitted through the weld is desired, the test sample 110 may be positioned such that the output beam of the pulsed-laser source is incident on one side of the weld 140 and the EMAT sensor 107 is positioned on the other side of the weld 140 and adjacent to the test sample 110, as shown in FIG. 2. Accordingly, it should be understood that the weld 140 is positioned between the point where the output beam 113 of the pulsed laser source 105 contacts the test sample 110 and the EMAT sensor 107. In this embodiment, the ultrasonic signals induced in the test sample 110 and received by the EMAT sensor 107 are transmitted through the weld 140. As defects alter the ultrasonic signal propagating through the weld the ultrasonic signal is transformed to an ultrasonic response signal which is received by the EMAT sensor 107. The ultrasonic response signal carries with it information concerning the presence of defects in the weld 140. Further, the ultrasonic response signal(s) may be correlated to a position along the length of weld 140 and test sample 110 based on the relative positioning between the test sample 110 and the point where the output beam of the pulsed laser source contacts the test sample 110 and/or the position of the EMAT sensor 107.

In another embodiment (not shown), when an acoustic response signal reflected by the weld is desired, the EMAT sensor may be positioned on one side of the weld and the output beam of the pulsed-laser source may be directed onto the test sample on the same side of the weld as the EMAT sensor. The ultrasonic response signal induced in the test sample by the pulsed-laser source propagates through the test sample to the weld which reflects at least a portion of the signal (e.g., the ultrasonic response signal), which is detected by the EMAT sensor. Because portions of the weld which contain defects reflect or transmit the ultrasonic signal differently than portions of the weld without defects, the reflected ultrasonic response signal received by the EMAT sensor carries with it information concerning the presence of defects in the weld.

Referring now to FIGS. 2 and 5-9, one embodiment of a method 200 for detecting the presence of defects in a weld with the defect detection system 150 is depicted. In a first step 202, the controller triggers the pulsed laser source 105 to induce an ultrasonic signal in the test sample 110 by directing a series of beam pulses onto the surface of the test sample, as described above. The controller may be programmed to trigger the pulsed laser source multiple times at each measurement location and the collected ultrasonic response signals generated by each firing of the pulsed laser at each measurement location may be averaged to increase the signal to noise ratio of the collected ultrasonic response signal at that location. In the embodiments described herein the pulsed laser source is operated in an ablative mode to induce ultrasonic response signals in the test sample which have frequency content from about 200 kHz to about 15 MHz. However, it should be understood that the pulsed laser source may also be operated in a thermoelastic mode to generate ultrasonic signals in the test sample. The ultrasonic signal propagates through the test sample 110 and the weld 140 and portions of the ultrasonic signal may be reflected by defects in the weld 140 or other features in the test sample while other portions of the ultrasonic response signal may be transmitted through the weld 140. In this example, the ultrasonic response signal is the signal transmitted or reflected after portions of the ultrasonic signal are reflected and/or defracted by defects and/or other features in the test sample.

In a second step 204, the ultrasonic response signal induced in the test sample 110 is collected with the EMAT sensor 107. In the embodiments described herein, the EMAT sensor 107 is positioned to collect an ultrasonic response signal which is transmitted through the weld 140, as illustrated in FIG. 2 and described above. The EMAT sensor 107 converts the collected ultrasonic response signal to an electrical signal which has a voltage proportional to the amplitude of the ultrasonic response signal. Accordingly, in the embodiments described herein where the collected ultrasonic response signal has been transmitted through the weld 140, electrical signals produced by the EMAT sensor 107 with relatively large voltages correspond to ultrasonic response signals with relatively greater amplitudes while electrical signals with relatively low voltages correspond to ultrasonic response signals with relatively lower amplitudes. The relative magnitude of the ultrasonic response signal may be generally indicative of the absence or presence of defects and/or manufacturing features in the test sample with lower amplitudes indicative of the presence of a defect and/or manufacturing feature and higher amplitudes indicative of the absence of a defect and/or manufacturing feature.

The electrical signal produced by the EMAT sensor 107 is transmitted from the EMAT sensor 107 to the controller (not shown) where the electrical signal is stored in a memory associated with the controller. The amplitude (i.e., the voltage) of the electrical signal is stored in the memory as a function of time and indexed or correlated to a specific position along the weld 140 of the test sample 110. Accordingly, it should be understood that the amplitude of the ultrasonic signal may be a function of both time (t) and position (x) along the weld 140 and, as such, may be written as $f(x,t)$.

After the collected ultrasonic signal is stored in memory for one measurement location along the weld 140, the position of the test sample 110 relative to the pulsed laser source 105 and EMAT sensor 107 may be adjusted such that ultrasonic sonic response signals may be induced and collected from the test sample 110 at a different measurement location along the weld 140. In the embodiment shown in FIG. 2, the position of the test sample 110 relative to the pulsed laser source 105 and EMAT sensor 107 may be adjusted by the controller which sends a control signal to the stepper motor (not shown) coupled to the lead screw 122. Rotation of the stepper motor causes the lead screw 122 to rotate, which, in turn, imparts translational motion to the sample stage 108 thereby adjusting the position of the test sample 110 relative to the pulsed laser source 105 and EMAT sensor 107.

Figure 6:
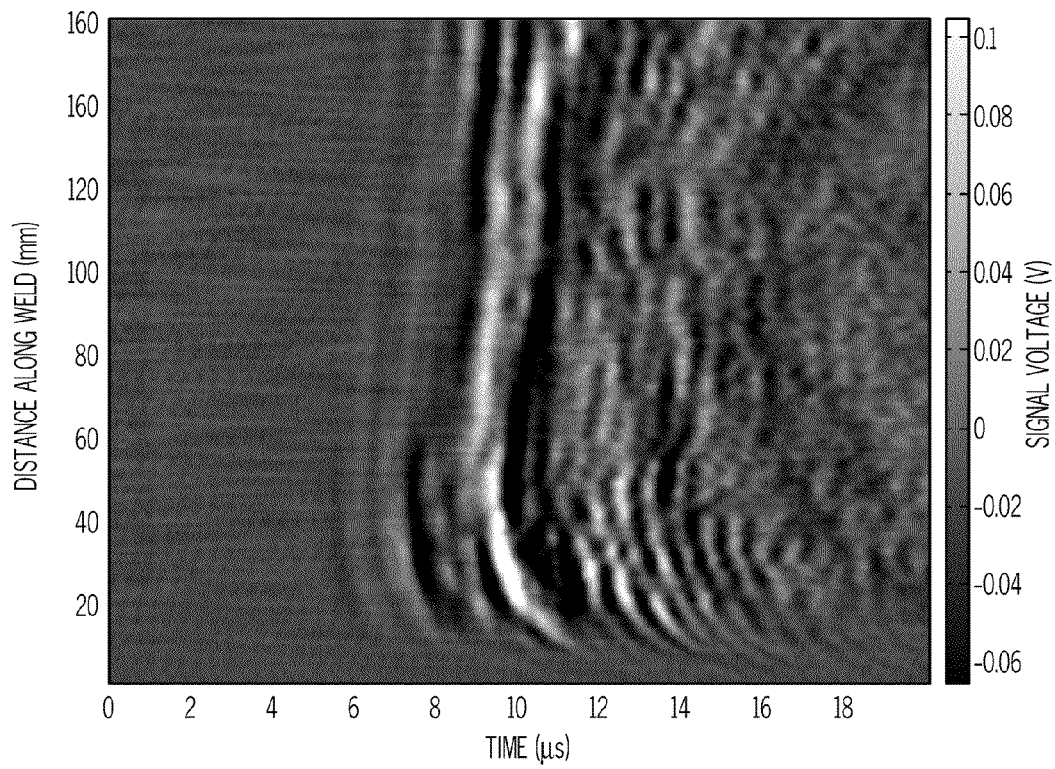
FIG. 6 is a plot of an ultrasonic response signal collected from a test sample according to one or more embodiments shown and described herein.

After the position of the test sample 110 has been adjusted, steps 202 and 204 may be repeated at a new location along the weld 140 and the amplitude of the ultrasonic response signal is stored in the memory operatively associated with the controller as a function of both time (t) and location (x) along the weld. This process of inducing an ultrasonic signal, collecting an ultrasonic response signal and adjusting the position of the test sample may be repeated multiple times to develop a set of ultrasonic response signals for a segment of the weld and/or the entire length of the weld 140. FIG. 6 graphically illustrates a set of ultrasonic response signals collected from one test sample. The y-axis is indicative of the position along the weld, the x-axis is indicative of the time interval over which the ultrasonic response signal was collected, and the gray scale is indicative of the relative amplitude of the collected ultrasonic response signal in units of voltage. The position of the test sample was adjusted in millimeter increments although larger or smaller increments may be used depending on the desired defect resolution.

Still referring to FIG. 6, the higher frequency/shorter wavelength content of the ultrasonic signals induced in the test sample may be more susceptible to diffraction and/or reflection by features in the test sample than other, lower frequencies. These features may include regular features (i.e., features regularly occurring in each of a plurality test samples) such as manufacturing features (e.g., connector holes, stamp marks, etc.) and irregular features such as defects. For example, one frequency range particularly susceptible to reflection and/or diffraction by these features may be from about 0.977 MHz to about 1.464 MHz. Accordingly, the corresponding frequencies in the ultrasonic response signal collected from the test sample may contain information regarding the presence of such features.

In step 206, the controller may be programmed to filter the ultrasonic response signals collected from the test sample to isolate frequencies most susceptible to reflection and/or diffraction by features such as manufacturing features and/or defects. In the embodiments described herein, the collected ultrasonic response signals for each measurement location (x) along the weld may be filtered into frequency ranges that are sensitive to features (such as defects) in the test sample by first decomposing the collected ultrasonic response signal by discrete wavelet transform (DWT). Specifically, for a specified location x along the weld, the collected ultrasonic response signal f(t) may be decomposed into a set of wavelet coefficients WS(h,k) according to the relationship:

$$WS(h,k) = \int f(t) \Psi_{h,k}^*(t) dt \qquad (1),$$

where $\Psi_{h,k}^*(t)$ is the complex conjugate of wavelet $\Psi_{h,k}(t)$. Wavelet $\Psi_{h,k}(t)$ may be a function of a mother wavelet function $\Psi$ which is scaled by scaling parameter $s_0^h$ and shifted by shifting parameter $k\tau_0 s_0^h$ such that:

$$\Psi_{h,k}(t) = \frac{1}{\sqrt{s_0^h}} \Psi\left(\frac{t - k\tau_0 s_0^h}{s_0^h}\right), \qquad (2)$$

where t is time and h and k are integers. $s_0$ is generally selected to be 2 and the shifting parameter $\tau_0$ is generally selected to be 1.

The selection of the mother wavelet $\Psi$ may depend on the shape or form of the collected ultrasonic response signal as a given ultrasonic response signal may be better approximated by a wavelet having a shape or form similar to that of the signal. The mother wavelet $\Psi$ used for decomposition of the ultrasonic response signal may be selected from, for example, the Daubechies wavelet family, the Coiflet wavelet family, the Haar wavelet family, the Symmlet wavelet family, the Discrete Meyer (DMEY) wavelet or similar wavelet families. For example, in one embodiment wavelet 6 of the Daubechies wavelet family may be used as the mother wavelet $\Psi$ to decompose the ultrasonic response signal. However, it should be understood that other mother wavelets may be used.

As indicated by Equation 1, decomposition of the ultrasonic response signal for each measurement location x by DWT produces a set of wavelet coefficients WS(h,k) for that measurement location. After decomposition, the controller may be programmed to band-pass filter each resulting set of wavelet coefficients to isolate a frequency range most sensitive to defects which, in the embodiments described herein, is from about 0.977 MHz to about 1.464 MHz. Filtering the set of wavelet coefficients is performed by zeroing elements of the wavelet coefficient WS(h,k) that correspond to frequency content outside the desired frequency range. In the embodiments described herein, decomposition by DWT and filtering may be performed by the controller using Mallet's filter banks algorithm which produces a band-pass filtered set of wavelet coefficients for each measurement location along the weld.

After each collected ultrasonic response signal is decomposed by DWT and the resulting wavelet coefficients are filtered to isolate the desired frequency content, the controller may be programmed to reconstruct a filtered response signal $f(x,t)$ for each measurement location from the corresponding filtered sets of wavelet coefficients by inverse discrete wavelet transform (IDWT) to form a filtered response signal for each measurement location x along the weld. For example, when there are 120 separate measurement locations along the weld, 120 filtered response signals are created by IDWT.

In a next step 208, the controller may be programmed to calculate and normalize an energy E(x) for each measurement location x on the test sample based on the corresponding filtered response signals $f(x,t)$ for the measurement location. The energy E(x) for each measurement location x may be calculated by summing the square of the corresponding filtered response signal $f(x,t)$ over the time duration of the signal such that:

$$E(x) = \sum_t (f(x, t))^2, \qquad (3)$$

where E(x) is the energy at location x and $f(x,t)$ is the amplitude of the filtered ultrasonic response signal at location x and time t.

Figure 7:
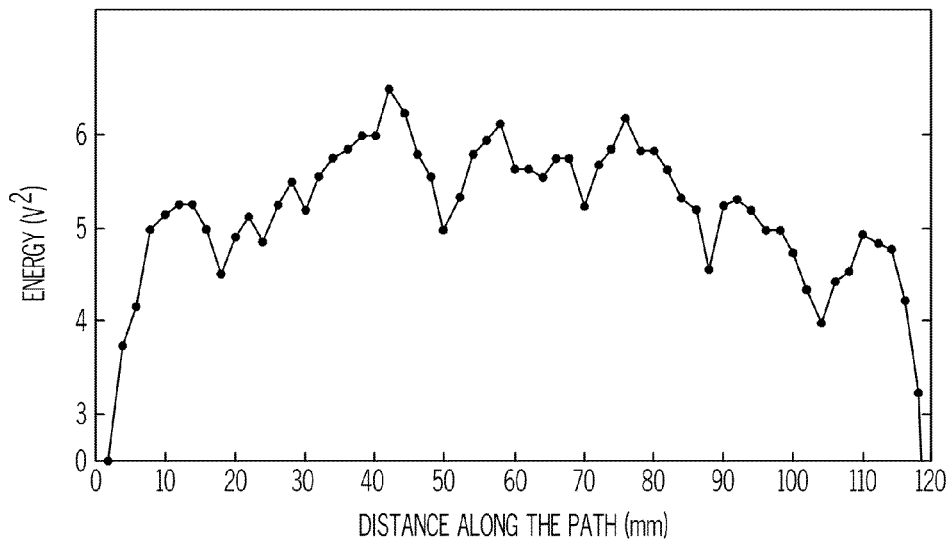
FIG. 7 is a plot of an energy distribution derived from the ultrasonic response signal of FIG. 6.

Based on the energy E(x) for each measurement location along the weld, an energy distribution may be plotted as depicted in FIG. 7 where the x-axis corresponds to the measurement location x along the weld and the y-axis corresponds to the ultrasonic signal energy E(x) for each measurement location. The plotted energy distribution shows that the energy of the ultrasonic response signal fluctuates along the length of the weld. These fluctuations in energy may be caused by the presence of various features in the test sample and/or weld which may reflect or diffract the ultrasonic signal induced in the test sample. Such features may include regular features, such as stamp marks, connector holes, and the like, or irregular features, such as defects and/or changes in the thickness of the weld, as described above.

Figure 5:
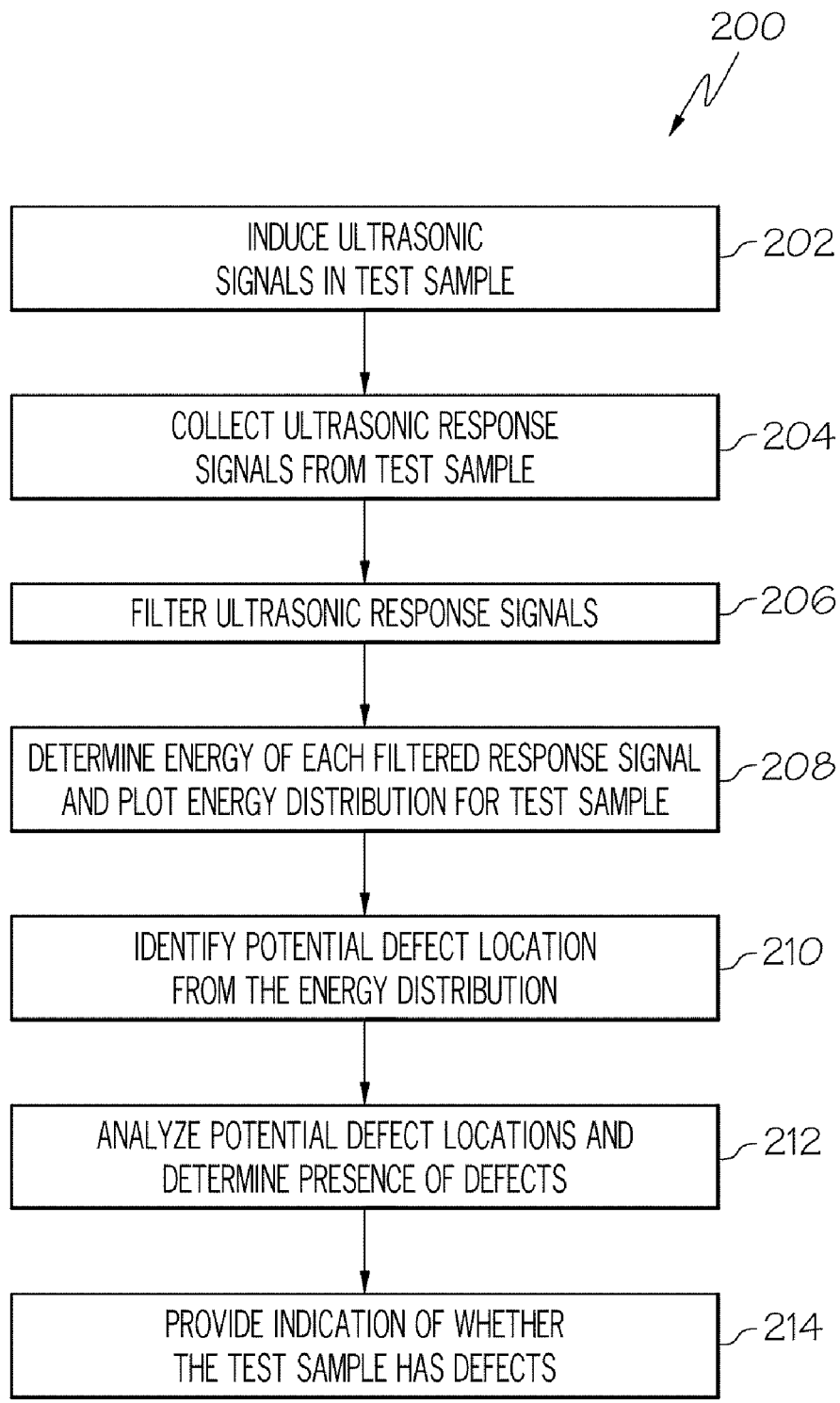
FIG. 5 is a flow diagram of a method for detecting defects in a welded structure according to one or more embodiments shown and described herein.
Figure 9:
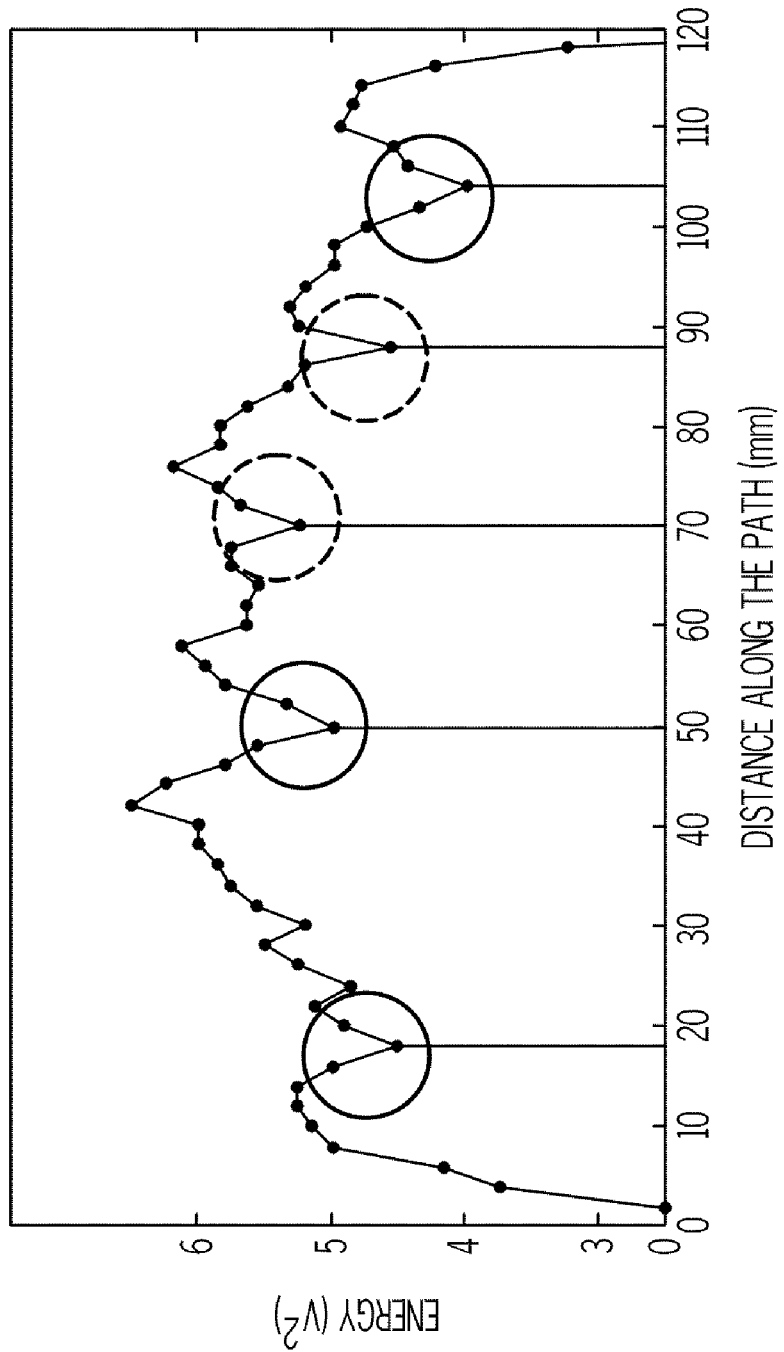
FIG. 9 is a plot of the energy distribution of FIG. 7 with potential defect locations identified.

Referring now to FIGS. 5, 7 and 9, in a next step 210, the controller may be programmed to identify potential defect locations along the weld utilizing the energy E(x) for each measurement location and/or a plotted energy distribution, such as the plotted energy distribution shown in FIG. 7. To identify potential defect locations, the controller may compare the energy E(x) for each measurement location x to the energy of adjacent measurement locations, such as, for example, measurement locations x−1 and x+1. If the energy E(x) is a local minimum (e.g., E(x−1)>E(x) and E(x+1)>E(x)) then measurement location x is a potential defect location. Examples of potential defect locations are indicated by the circled points in the plotted energy distribution shown in FIG. 9. Where E(x) is a local minimum, the controller may designate the position x of the local minimum as a potential defect location $x_{pd}$ and stores the potential defect location $x_{pd}$ in a memory operably associated with the controller.

Referring now to FIGS. 5 and 7-9, in a next step 212, the controller may be programmed to analyze fluctuations in the ultrasonic energy at measurement locations neighboring each potential defect location $x_{pd}$ to determine the presence of defects in the weld utilizing the energy $E(x_{pd})$ of the potential defect location $x_{pd}$ and the energy of neighboring measurement locations. In one embodiment, the controller may analyze each potential defect location $x_{pd}$ for the presence of defects by comparing the energy $E(x_{pd})$ of the potential defect location and the energy of adjacent measurement locations to a set of defect energy patterns, such as the exemplary defect energy patterns graphically depicted in FIGS. 8A-8J, which may be stored in the memory operatively associated with the controller.

The defect energy patterns shown in FIGS. 8A-8J may be derived from test samples which have been destructively examined after ultrasonic signals have been induced in the test samples and ultrasonic response signals have been collected from the test samples, as described above. An energy distribution for each test sample may then be plotted and the results of the destructive examination of each test sample may be compared to the corresponding energy distribution to correlate fluctuations in the energy distribution to the defects identified through destructive examination. Based on these comparisons a set of defect energy patterns may be identified which correspond to fluctuations in the energy distribution caused by the defects. Further, the results of the destructive examination may be used to correlate specific defect energy patterns to specific defect types (e.g., short legs, blow holes, lack of penetration, etc.).

In order to determine if a potential defect location $x_{pd}$ contains an actual defect, the controller compares the pattern formed by the energy $E(x_{pd})$ of each potential defect location $x_{pd}$ and the energy of neighboring measurement locations on each side of the potential defect location $x_{pd}$ to the defect energy patterns and, if the patterns have a similar shape, the controller designates the potential defect location $x_{pd}$ as a defect location $x_D$ and stores this location as a defect location in the memory operatively associated with the controller.

Referring to FIGS. 8 and 9 by way of example, a potential defect location $x_{pd}$ is present at x=104 mm. The pattern formed by the energy $E(x_{pd})$ of this potential defect location and the energy of measurement locations on each side of the potential defect location (e.g., the 3 measurement locations to the left of x=104 mm and the three measurement locations to the right of x=104 mm) form a pattern similar to the defect energy pattern of FIG. 8I and, as such, the controller identifies the potential defect location at x=104 mm as a defect location $x_D$ and stores this location in memory as a defect.

In an alternative embodiment, at step 212, the controller may be programmed to analyze each potential defect location $x_{pd}$ by comparing the energy E(x) at each potential defect location $x_{pd}$ to the energy of a plurality of neighboring measurement locations. The controller may compare the energy for potential defect location $x_{pd}$ to the energy for at least two consecutive measurement locations on each side of the potential defect location $x_{pd}$. For example, the controller may compare the energy for points $x_{pd}-1, x_{pd}-2 \ldots x_{pd}-i$ on one side of $x_{pd}$, and to points $x_{pd}+1, x_{pd}+2 \ldots x_{pd}+j$ on the other side of $x_{pd}$, where i and j are integers, $i<x_{pd}$ and $1\leq j\leq n-x_{pd}$ and n is the total number of measurement locations along the weld.

If the ultrasonic energy on each side of the potential defect location increases monotonically for each of the neighboring measurement locations, and if the number of neighboring measurement locations with monotonically increasing energy is between two and four on each side of the defect location, then the controller identifies the potential defect location $x_{pd}$ as a defect location $x_D$ and stores the location in a memory operatively associated with the controller. As shown in FIG. 9, locations enclosed by a solid circle (e.g., at x=18 mm, 50 mm and 104 mm) are indicative of defect locations and the locations enclosed by a dashed circle (e.g., at x=70 mm and 88 mm) are potential defect locations which, after further analysis by the controller, do not meet the criteria for the presence of a defect (i.e., the ultrasonic energy does not increase monotonically over at least two neighboring measurement locations or it increases monotonically over more than four neighboring measurement locations on each side of the potential defect location).

Figure 8A:
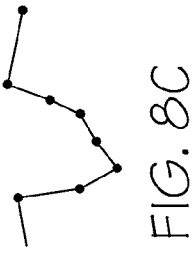
FIGS. 8A-8J schematically depict defect energy patterns which may be used to identify the presence of defects in a weld by comparison to an energy distribution, such as the energy distribution of FIG. 7, according to one or more embodiments shown and described herein.
Figure 8B:
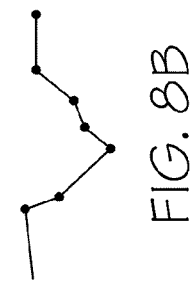
Figure 8C:
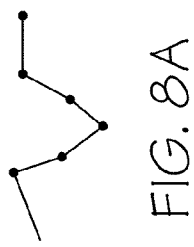
Figure 8D:
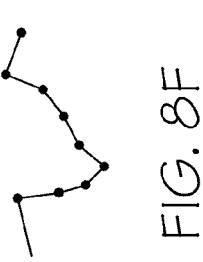
Figure 8E:
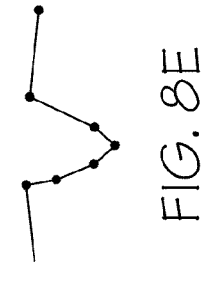
Figure 8F:
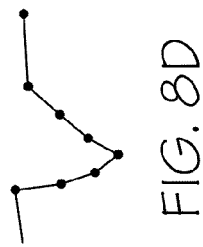
Figure 8G:
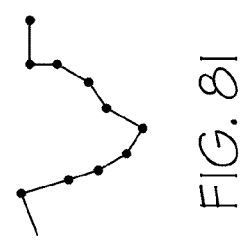
Figure 8H:
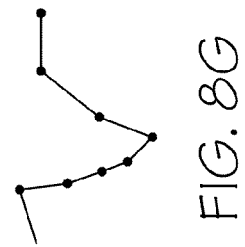
Figure 8I:
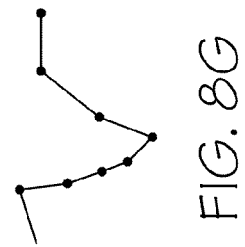
Figure 8J:
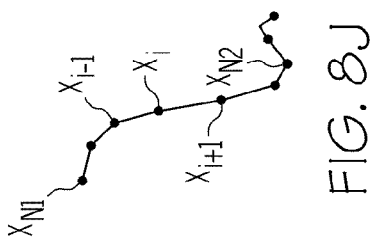

In one embodiment, after the ultrasonic energy of the potential defect location is compared to at least two neighboring defect locations on each side of the potential defect location to determine if the ultrasonic energy increases monotonically, the energy of the potential defect location and the energy of neighboring measurement locations may be compared to defect energy patterns stored in memory, as described above, to further assess whether the potential defect location contains a particular defect, such as, for example, a lack of penetration defect which has a defect energy pattern as shown in FIG. 8J. If the ultrasonic energy at the potential defect location and the ultrasonic energy at the neighboring defect locations corresponds to a defect energy pattern, then the controller designates the potential defect location $x_{pd}$ as a defect location $x_D$ and stores the location in memory as a defect.

In one embodiment, in order to identify a lack of penetration defect such as that shown in FIG. 8J, the controller may be programmed to first identify local maximum and minimum pairs by comparing the energy of each measurement location to the energy of neighboring measurement locations. For example, the points $X_{N1}$ and $X_{N2}$ shown in FIG. 8J are indicative of local maximum and minimum, respectively. Thereafter, the average slope between the local maximum and minimum may be determined utilizing the following equation:

$$slope_{avg} = \frac{E(X_{N2}) - E(X_{N1})}{X_{N2} - X_{N1}}, \quad (4)$$

where $E(X_{N2})$ is the energy at measurement location $X_{N2}$ and $E(X_{N1})$ is the energy at measurement location $X_{N1}$.

Thereafter, for each point $X_i$ between $X_{N1}$ and $X_{N2}$, the controller may be programmed to determine the slope between points $X_i$ and $X_{i-1}$ and the slope between points $X_i$ and $X_{i-1}$ and compare each slope to the averaged slope. If the absolute value of the slope between points points $X_i$ and $X_{i-1}$ and the absolute value of the slope between points $X_i$ and $X_{i+1}$ are both greater than the average slope, then the point $X_i$ is a defect location.

In yet another embodiment, at step 212, the controller may be programmed to analyze each potential defect location $x_{pd}$ by comparing the energy $E(x)$ at each potential defect location $x_{pd}$ to the energy of a plurality of neighboring measurement locations, as described above. When the energy on each side of the potential defect location increases monotonically for each of the neighboring measurement locations, the controller identifies the potential defect location $x_{pd}$ as a defect location $x_D$ and stores the location in a memory operatively associated with the controller. The controller may then be programmed to compare the pattern formed by the energy $E(x_D)$ of each defect location $x_D$ and the energies of neighboring measurement locations to defect energy patterns stored in memory to identify the specific types of defects which may be present in the weld.

In step 214, the controller may provide a visual and/or audible indication of the presence of defects in the weld. In one embodiment, where the defect detection system 150 comprises a display, the controller may be programmed to plot an energy distribution on the display similar to that shown in FIG. 7. The controller may also be programmed to identify defect locations on the display. For example, where the controller is programmed to display a plot of the energy distribution on the display, the controller may be programmed to graphically indicate the location $x_D$ of defects on the energy distribution. Alternatively or additionally, the controller may be programmed to display the location of each defect. For example, referring to the plot of the energy distribution shown in FIG. 9, the controller may be operable to indicate on the display that defects are present in the weld at x=18 mm, 50 mm and 104 mm.

It should now be understood that the defect detection system and methods shown and described herein may be used to determine the presence and location of defects in a weld utilizing ultrasonic signals. The system may be implemented in a manufacturing environment to perform automated inspection of welded structures of various configurations. The system may be used as a quality control tool for each welded structure produced or, alternatively, to analyze a random sampling of the welded structures produced.

While the defect detection systems described herein utilize non-contact methods for inducing an ultrasonic signal in the test sample and collecting an ultrasonic response signal from the test sample, it should be understood that the methods utilized by the defect detection systems may also be used by ultrasonic inspection systems which utilize acoustic signal generators and/or acoustic signal detectors which physically contact the test sample.

Further, while the methods for analyzing the ultrasonic response signals collected from the test sample are described herein as being performed in conjunction with inducing an ultrasonic signal in the test sample and collecting ultrasonic response signals from the test sample, it should be understood that the method for analyzing the ultrasonic response signals may be performed independently from the steps of inducing an ultrasonic signal and collecting an ultrasonic response signal. For example, the collected ultrasonic response signals may be stored in the controller and analyzed according to the methods described herein at a later time.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for determining if a defect is present in a weld from ultrasonic response signals collected from a plurality of measurement locations along a weld, the method comprising:
   filtering an ultrasonic response signal from each of the measurement locations to produce a filtered response signal for each of the measurement locations;
   calculating an ultrasonic energy for each of the measurement locations with the corresponding filtered response signal;
   comparing the ultrasonic energy for each measurement location to the ultrasonic energy of adjacent measurement locations to identify potential defect locations, wherein, when the ultrasonic energy of a measurement location is less than the ultrasonic energy of the adjacent measurement locations, the measurement location is a potential defect location; and
   analyzing fluctuations in the ultrasonic energy at measurement locations neighboring the potential defect locations to determine if a defect is present in the weld, wherein fluctuations in the ultrasonic energy are analyzed by comparing the ultrasonic energy of a potential defect location to the ultrasonic energy of a plurality of measurement locations on each side of the potential defect location, wherein, when the ultrasonic energy increases monotonically over the plurality of measurement locations on each side of the potential defect location, the potential defect location comprises a defect.

2. The method of claim 1 wherein the ultrasonic response signal from each of the measurement locations is filtered by:
   decomposing the ultrasonic response signal by discrete wavelet transform to produce a set of wavelet coefficients for the ultrasonic response signal;
   band-pass filtering the set of wavelet coefficients to isolate a frequency range sensitive to defects in the weld; and
   producing the filtered response signal for the measurement location by performing inverse discrete wavelet transform on the corresponding filtered set of wavelet coefficients.

3. The method of claim 1 wherein, when the potential defect location comprises a defect, the ultrasonic energy of the potential defect location and the ultrasonic energy of measurement locations neighboring the potential defect location are compared to defect energy patterns to determine what type of defect is present in the weld.

4. The method of claim 1 wherein fluctuations in the ultrasonic energy are analyzed by comparing the ultrasonic energy of a potential defect location and the ultrasonic energy of measurement locations neighboring the potential defect location to defect energy patterns to determine if the potential defect location comprises a defect.

5. A method for testing a weld for defects, the method comprising:
   inducing ultrasonic signals at multiple measurement locations along the weld;
   collecting an ultrasonic response signal for each of the measurement locations;
   filtering the ultrasonic response signal from each of the measurement locations to produce a filtered response signal for each of the measurement locations;
   calculating an ultrasonic energy for each of the measurement locations with the corresponding filtered response signal;
   determining an ultrasonic energy distribution for the weld based on the ultrasonic energy for each of the measurement locations;
   identifying local minima in the ultrasonic energy distribution; and
   analyzing fluctuations in the ultrasonic energy distribution around each local minimum to determine if a defect is present in the weld, wherein fluctuations in the ultrasonic energy distribution around a local minimum are analyzed by comparing the ultrasonic energy of the local minimum to the ultrasonic energy of a plurality of measurement locations on each side of the local minimum, wherein, when the ultrasonic energy distribution increases monotonically at the plurality of measurement locations on each side of the local minimum, the local minimum is a defect location.

6. The method of claim 5 wherein the ultrasonic response signal from each of the measurement locations is filtered by:
   decomposing the ultrasonic response signal by discrete wavelet transform to produce a set of wavelet coefficients for the ultrasonic response signal;
   band-pass filtering the set of wavelet coefficients to isolate a frequency range sensitive to defects in the weld; and
   producing the filtered response signal for a measurement location by performing inverse discrete wavelet transform on the filtered set of wavelet coefficients.

7. The method of claim 5 wherein, when the local minimum is a defect location, the ultrasonic energy of the local minimum and the ultrasonic energy of measurement locations neighboring the local minimum are compared to defect energy patterns to determine what type of defect is present in the weld.

8. The method of claim 5 wherein fluctuations in the ultrasonic energy distribution are analyzed by comparing the ultrasonic energy of a local minimum and the ultrasonic energy of measurement locations neighboring the local minimum to defect energy patterns to determine if a defect is present in the weld at the local minimum.

9. The method of claim 5 wherein the ultrasonic response signal for each measurement location is filtered to isolate a frequency range from about 0.977 MHz to about 1.464 MHz.

10. The method of claim 5 wherein ultrasonic signals are induced by directing an output beam of a pulsed laser source on to a surface of a test sample in which the weld is located.

11. The method of claim 5 wherein:
   a plurality of ultrasonic signals are induced in the weld at each of the measurement locations; and
   a plurality of ultrasonic response signals are collected at each of the measurement locations and averaged.

12. A defect detection system for identifying defects in a weld, the defect detection system comprising a controller, an acoustic signal generator, an acoustic signal detector, and a positioning device, wherein the acoustic signal generator, the acoustic signal detector and the positioning device are electrically coupled to the controller and the controller is programmed to:
   induce ultrasonic signals at multiple measurement locations along the weld with the acoustic signal generator;
   collect an ultrasonic response signal from each of the measurement locations with the acoustic signal detector and store each ultrasonic response signal in a memory operatively associated with the controller;
   filter the ultrasonic response signal from each of the measurement locations to produce a filtered response signal for the corresponding measurement locations;
   calculate an ultrasonic energy for each of the measurement locations with the corresponding filtered response signal;
   compare the ultrasonic energy for each measurement location to the ultrasonic energy of adjacent measurement locations to identify potential defect locations, wherein, when the ultrasonic energy of a measurement location is less than the ultrasonic energy of the adjacent measurement locations, the measurement location is a potential defect location; and
   analyze fluctuations in the ultrasonic energy at measurement locations neighboring the potential defect locations to determine if a defect is present in the weld, wherein the controller is programmed to analyze fluctuations in the ultrasonic energy by comparing the ultrasonic energy of a potential defect location to the ultrasonic energy of a plurality of measurement locations on each side of the potential defect location, wherein, when the ultrasonic energy increases monotonically over the plurality of measurement locations on each side of the potential defect location, the potential defect location comprises a defect.

13. The defect detection system of claim 12 wherein the controller is programmed to filter the ultrasonic response signal from each of the measurement locations by:
   decomposing the ultrasonic response signal by discrete wavelet transform to produce a set of wavelet coefficients for the ultrasonic response signal;
   band-pass filtering the set of wavelet coefficients to isolate a frequency range sensitive to defects in the weld; and
   producing the filtered response signal for the measurement location by performing inverse discrete wavelet transform on the filtered set of wavelet coefficients.

14. The defect detection system of claim 12 wherein, when the potential defect location comprises a defect, the controller is programmed to compare the ultrasonic energy of the potential defect location and the ultrasonic energy of measurement locations neighboring the potential defect location to defect energy patterns to determine what type of defect is present in the weld.

15. The defect detection system of claim 12 wherein the controller is programmed to analyze fluctuations in the ultrasonic energy by comparing the ultrasonic energy of a potential defect location and the ultrasonic energy of measurement locations neighboring the potential defect location to defect energy patterns to determine if the potential defect location comprises a defect.

16. The defect detection system of claim 12 wherein the acoustic signal generator is a pulsed laser source.

17. The defect detection system of claim 12 wherein the acoustic signal detector is an EMAT sensor.

* * * * *